US012410470B2

(12) United States Patent
Acharya et al.

(10) Patent No.: US 12,410,470 B2
(45) Date of Patent: *Sep. 9, 2025

(54) DETECTION OF SEQUENCES UNIQUELY ASSOCIATED WITH A DNA TARGET REGION

(71) Applicant: PIONEER HI-BRED INTERNATIONAL, INC., Johnston, IA (US)

(72) Inventors: Ananta Acharya, Johnston, IA (US); Amanda Marie Gannon, Dallas Center, IA (US); Hena Guo, Johnston, IA (US); Kevin Hayes, Urbandale, IA (US); Robyn Lynn Laskowski, Des Moines, IA (US); Robert Ebow McEwan, Ankeny, IA (US); Carisa Townsend, Palmetto, GA (US); Lasantha Ubayasena, West Lafayette, IN (US); Gina Marie Zastrow-Hayes, Urbandale, IA (US)

(73) Assignee: PIONEER HI-BRED INTERNATIONAL, INC., Johnston, IA (US)

( * ) Notice: Subject to any disclaimer, the term of this patent is extended or adjusted under 35 U.S.C. 154(b) by 147 days.

This patent is subject to a terminal disclaimer.

(21) Appl. No.: 17/754,890

(22) PCT Filed: Oct. 9, 2020

(86) PCT No.: PCT/US2020/055079
§ 371 (c)(1),
(2) Date: Apr. 14, 2022

(87) PCT Pub. No.: WO2021/076423
PCT Pub. Date: Apr. 22, 2021

(65) Prior Publication Data
US 2024/0093315 A1    Mar. 21, 2024

(51) Int. Cl.
| | | |
|---|---|---|
| *C12Q 1/6869* | (2018.01) | |
| *C12Q 1/6806* | (2018.01) | |
| *C12Q 1/6851* | (2018.01) | |
| *C12Q 1/6853* | (2018.01) | |
| *C12Q 1/6855* | (2018.01) | |
| *C12Q 1/6858* | (2018.01) | |
| *C12Q 1/686*  | (2018.01) | |
| *C12Q 1/6874* | (2018.01) | |
| *C12Q 1/6895* | (2018.01) | |

(52) U.S. Cl.
CPC ......... *C12Q 1/6869* (2013.01); *C12Q 1/6806* (2013.01); *C12Q 1/6851* (2013.01); *C12Q 1/6853* (2013.01); *C12Q 1/6855* (2013.01); *C12Q 1/6858* (2013.01); *C12Q 1/686* (2013.01); *C12Q 1/6874* (2013.01); *C12Q 1/6895* (2013.01); *C12Q 2525/155* (2013.01); *C12Q 2525/179* (2013.01); *C12Q 2525/185* (2013.01); *C12Q 2525/191* (2013.01); *C12Q 2537/149* (2013.01); *C12Q 2549/00* (2013.01); *C12Q 2600/156* (2013.01); *C12Q 2600/172* (2013.01)

(58) Field of Classification Search
CPC ............... C12Q 1/6869; C12Q 1/6806; C12Q 1/6853; C12Q 1/686; C12Q 2525/155; C12Q 2525/179; C12Q 2525/191; C12Q 2537/149; C12Q 2563/179; C12Q 2535/122; C12Q 2525/185
See application file for complete search history.

(56) References Cited

U.S. PATENT DOCUMENTS

| | | |
|---|---|---|
| 8,785,353 B2 | 7/2014 | Van Eijk et al. |
| 9,797,001 B2 | 10/2017 | Beatty et al. |
| 10,095,832 B2 | 10/2018 | Van Eijk et al. |
| 10,316,364 B2 | 6/2019 | Van Eijk et al. |
| 10,544,448 B2 | 1/2020 | Dotson et al. |
| 10,544,471 B2 | 1/2020 | Dotson et al. |
| 10,550,424 B2 | 2/2020 | Dotson et al. |
| 10,927,409 B1 | 2/2021 | Acharya et al. |
| 2009/0098555 A1 | 4/2009 | Roth |
| 2014/0315726 A1 | 10/2014 | Beatty et al. |
| 2016/0289669 A1 | 10/2016 | Fan et al. |
| 2016/0319345 A1 | 11/2016 | Gnerre et al. |
| 2017/0314067 A1 | 11/2017 | Shum et al. |
| 2019/0017113 A1 | 1/2019 | Corioni et al. |

(Continued)

FOREIGN PATENT DOCUMENTS

| | | |
|---|---|---|
| WO | 2016004368 A2 | 1/2016 |
| WO | 2016176091 A1 | 11/2016 |

(Continued)

OTHER PUBLICATIONS

Clevenger et al. Single Nucleotide Polymorphism Identification in Polyploids: A Review, Example, and Recommendations. Molecular Plant 2015; 8: 831-846 (Year: 2015).*
Weeks, D.P. Gene editing in polyploid crops: wheat, camelina, canola, potato, cotton, peanut, sugar cane, and citrus. Progress in Molecular Biology and Translational Science 2017; 149: 65-80 (Year: 2017).*
Arulandhu, Alfred J.; et al.: "NGS-based amplicon sequencing approach; towards a new era in GMO screening and detection", Food Control, 2018, vol. 93, pp. 201-210.
Baetens, Machteld; et al.; "Applying Massive Parallel Sequencing to Molecular Diagnosis of Marfan and Loeys-Dietz Syndromes", Human Mutation, May 3, 2011 (May 3, 2011), vol. 32, No. 9, pp. 1053-1062.

(Continued)

*Primary Examiner* — Angela M. Bertagna

(57) ABSTRACT

The disclosed embodiments concern methods for determining sequences of interest using targeted unique molecular index (TUMI) sequences that are uniquely associated with individual polynucleotide fragments in plants, such as those present in a transgenic event, a site-specific mutation or a wild type variant. System, apparatus, and computer program products are also provided for determining a sequence of interest implementing the methods disclosed.

21 Claims, 6 Drawing Sheets

(56) References Cited

U.S. PATENT DOCUMENTS

2019/0078148 A1    3/2019  Zheng
2019/0106729 A1    4/2019  Pel et al.
2019/0119742 A1    4/2019  Zhang
2019/0147977 A1    5/2019  Van Eijk et al.

FOREIGN PATENT DOCUMENTS

WO         2018136248 A1      7/2018
WO    WO-2019195166 A1 *  10/2019  ......... C12N 15/1075
WO         2020/169830 A1     8/2020

OTHER PUBLICATIONS

Brownie, Jannine; et al.; "The elimination of primer-dimer accumulation in PCR", Nucleic Acids Research, Jun. 27, 1997 (Jun. 27, 1997), vol. 25, No. 16, pp. 3235-3241.
Seitz, Volkhard; et al.; "A new method to prevent carry-over contaminations in two-step PCR NGS library preparations", Nucleic Acids Research, Jul. 7, 2015 (Jul. 7, 2015), vol. 43, No. 20, pp. 1-9.
Tu; et al.; BMC Genomics 2015; 13: 43. (Year: 2015).
International Search Report and Written Opinion for International Application No. PCT/US20/55079, Mailed Jan. 12, 2021.
International Preliminary Report on Patentability for International Application No. PCT/US2020/55079, mailed Apr. 28, 2022, 9 Pages.

* cited by examiner

DETECTION OF SEQUENCES UNIQUELY ASSOCIATED WITH A DNA TARGET REGION

BACKGROUND

Plants are being produced with an increasing number of transgenic traits and other nucleotide regions of interest, and there is a need in agricultural research to quickly and accurately detect these nucleotide regions of interest. Next generation sequencing technology is providing a higher volume of sequence information at increasingly higher speeds. While a direct sequencing approach may seem like a straightforward solution to plant sequencing, the size and complexity of plant genomes make targeted approaches more desirable for both cost and accuracy. Therefore, it is desirable to develop methods for detecting a large number of transgenic traits and other nucleotide regions of interest with a high degree of accuracy without direct sequencing.

SUMMARY

The disclosed implementations concern methods, apparatus, systems, and computer program products for determining the presence or absence of targeted nucleotide regions of interest using targeted unique molecular index (TUMI). These TUMI sequences may also be used in combination with sample index sequences to pool multiple TUMI containing amplicons into one sample set for sequencing.

The methods employ a placement and orientation of the TUMI and a sequencing primer binding site on a PCR amplicon that will initiate sequencing of the amplicon in a direction away from the targeted nucleotide regions of interest. This results in detecting only the TUMI without requiring the sequencing of the targeted nucleotide region of interest. Sequencing the shorter read of the TUMI sequence has the advantages of being faster, more accurate and a more efficient use of reagents.

The methods may be used for detecting native traits, transgenes, CRISPR modified sequences and viral sequences in crop breeding, seed production and grain production. The method has application in agriculture to detect sequences across a range of agricultural organisms, including agricultural crops, microbes, soil fungi, endophytes and plant symbiotic organisms. The method may also be used with any type of organism to detect nucleotide sequences, including humans, other mammals, reptiles, fish and any other type of single or multicellular organism. In some embodiments, the sensitivity of the method can be further enhanced to detect sequences present at only very low levels.

For transgenic sequences, the methods allow for universal TUMI to be used across the agricultural supply chain, e.g. seed research, seed production purity testing, grain production, grain storage and shipping. For example, a specific TUMI sequence may be used as the single detection sequence for a specific transgenic trait across each of these activities. In addition, the methods allow for the use of transgenic trait detection and genomic targeted markers in the same analysis platform without generating the nucleotide sequence information of the regulated genomic regions of breeding populations.

One embodiment of the method includes hybridizing a portion of a first PCR primer strand to all or part of a targeted nucleotide region of interest, said first PCR primer strand comprising a PCR forward primer, a TUMI uniquely associated with the targeted nucleotide region of interest, and a sequencing primer binding site oriented to initiate the sequencing reaction in the direction of the TUMI and away from the targeted nucleotide region of interest. The first PCR primer strand is paired with a second PCR primer strand that also hybridizes to all or part of the targeted nucleotide region of interest, said second PCR primer strand comprising a PCR reverse primer. The TUMI and sequencing primer binding site may instead (or also) be placed on the second PCR primer strand, as long as the sequencing primer binding site is positioned on the amplicon to be sequenced between the targeted nucleotide region of interest and the TUMI sequence, so that only the TUMI sequence will be determined during sequencing.

In another embodiment, the method comprises the addition of a sample index to a construct comprising the first PCR primer, or the second PCR primer, and, optionally, positioning the sample index in the same orientation as the TUMI sequence, so that both sequences are amplified and read without amplification of the targeted nucleotide region of interest.

A further aspect relates to a computer program product including a non-transitory machine readable medium storing program code that, when executed by one or more processors of a computer system, causes the computer system to implement a method for determining sequence information of a sequence of interest using the TUMI. The program code includes: (a) code for obtaining reads of a plurality of amplified polynucleotides, wherein the plurality of amplified polynucleotides are obtained by amplifying a TUMI sequence without amplifying a targeted nucleotide region of interest; and (b) code for associating the TUMI sequence with the targeted nucleotide region of interest.

One embodiment of the method involves detecting a targeted nucleotide region of interest in a plant genome by directional nucleotide sequencing, comprising hybridizing a nucleotide fragment comprising a sequencing primer binding site and a molecular sequence uniquely associated with the targeted nucleotide region of interest to the targeted nucleotide region of interest, wherein the sequencing primer binding site is positioned between the molecular sequence uniquely associated with the targeted nucleotide region of interest and the targeted nucleotide region of interest, performing PCR to create one or more amplicons comprising the sequencing primer binding site, the molecular sequence uniquely associated with the targeted nucleotide region of interest, and the targeted nucleotide region of interest, and sequencing one or more amplicons in a direction away from the targeted nucleotide region of interest so that the molecular sequence uniquely associated with the targeted nucleotide region of interest is sequenced without sequencing the targeted nucleotide region of interest. The targeted nucleotide region of interest may be any type of nucleotide sequence, including but not limited to a transgene, a native trait, a molecular marker, a gene coding region and a non-coding region. In embodiments of the method for detecting transgenes, two or more transgenes may be detected in the same reaction at the same time, and transgene stacks may be detected by using one or more TUMI.

In one embodiment, a first PCR primer strand is hybridized to the targeted nucleotide region of interest, said first PCR primer strand comprising, a first PCR primer, the molecular sequence uniquely associated with the targeted nucleotide region of interest, the sequencing primer binding site, and a first nucleotide sequence complement that will hybridize the first PCR primer strand to the targeted nucleotide region of interest, a second PCR primer strand is hybridized to the targeted nucleotide region of interest, said second PCR primer strand comprising a second PCR primer and a second nucleotide sequence complement that will hybridize the second PCR primer strand to the targeted nucleotide region of interest, a PCR is performed to create one or more amplified DNA sequences comprising the molecular sequence uniquely associated with the targeted nucleotide region of interest, the sequencing primer binding site and the targeted nucleotide region of interest, and the one or more amplified DNA sequences are sequenced in a sequencing reaction that starts at the sequencing primer binding site and proceeds in a direction toward and through the molecular sequence uniquely associated with the targeted nucleotide region of interest and away from the targeted nucleotide region of interest.

In certain embodiments, two PCR reactions may be utilized, and one or more sequencing adapters may be attached to the ends of the one or more amplified DNA sequences through a second PCR reaction performed prior to the sequencing reaction. In certain embodiments one or more sample indices are present on the one or more amplified DNA sequences. The sample indices may be added as part of the primer strands used in the first PCR reaction, the second PCR reaction, or both if two sample indices are desired. As with the other embodiments, the targeted nucleotide region of interest may be any type of nucleotide sequence, including but not limited to a transgene, a native trait, a molecular marker, a gene coding region and a non-coding region. In embodiments of the method for detecting transgenes, two or more transgenes may be detected in the same reaction at the same time, and transgene stacks may be detected by using one or more TUMI. The nucleotide sequence complements that are used to hybridize one or more PCR primer strands to the targeted nucleotide region of interest may hybridize to a sequence that spans a border sequence between the native plant genomic DNA and the targeted nucleotide region of interest or to a sequence within the targeted nucleotide region of interest.

One embodiment involves a system for detecting a targeted nucleotide region of interest in a plant genome by one directional nucleotide sequencing comprising a first PCR primer strand, wherein said first PCR primer strand may be hybridized to a targeted nucleotide region of interest, said first PCR primer strand comprising, a first PCR primer, a molecular sequence uniquely associated with the targeted nucleotide region of interest, a sequencing primer binding site, and a first nucleotide sequence complement that will hybridize the first PCR primer strand to the targeted nucleotide region of interest, wherein the sequencing primer binding site is positioned between the targeted nucleotide region of interest and the molecular sequence uniquely associated with the targeted nucleotide region of interest, and a second PCR primer strand, wherein said second PCR primer strand is hybridized to the targeted nucleotide region of interest, said second PCR primer strand comprising a second PCR primer and a second nucleotide sequence complement that will hybridize the second PCR primer strand to the targeted nucleotide region of interest. In one embodiment, a third PCR primer strand and a fourth PCR primer strand may be utilized in a subsequent PCR reaction, and said third PCR primer strand and said fourth PCR primer strand may each comprise sequencing adapters and/or a sample index. The nucleotide sequence complements that are used to hybridize one or more PCR primer strands to the targeted nucleotide region of interest may hybridize to a sequence that spans a border sequence between the native plant genomic DNA and the targeted nucleotide region of interest or to a sequence within the targeted nucleotide region of interest. The targeted nucleotide region of interest may be any type of nucleotide sequence, including but not limited to a transgene, a native trait, a molecular marker, a gene coding region and a non-coding region. An allelic variation or haplotype may be detected. In embodiments of the method for detecting transgenes, two or more transgenes may be detected in the same reaction at the same time, and transgene stacks may be detected by using one or more TUMI.

Detection may be quantitative, detecting the number of copies of the target nucleotide region of interest, or qualitative, in which presence or absence of the target nucleotide region of interest is detected.

DETAILED DESCRIPTION

Figure 1:
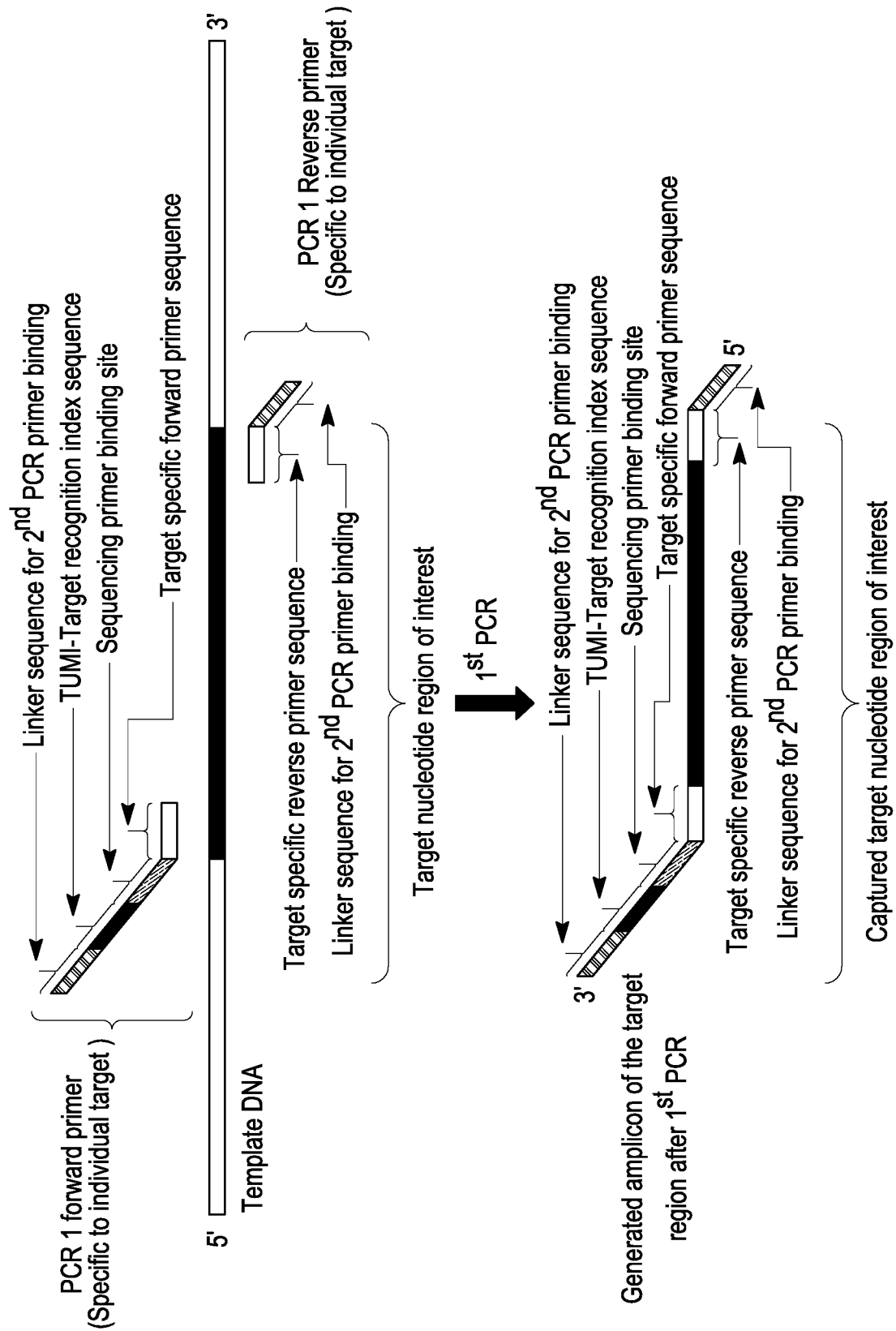
FIG. 1 Schematic diagram of the generation of an amplicon from a first PCR reaction that comprises a sequencing primer binding site positioned in between the TUMI sequence and the targeted nucleotide region of interest.

The disclosure concerns methods, apparatus, systems, and computer program products for sequencing nucleic acids, especially plant nucleic acids. The methods, apparatus, systems and computer programs have application for detecting regulated transgenic events, genetic modifications such as CRISPR induced modifications and native trait variation.

Unless otherwise indicated, the practice of the methods and systems disclosed herein involves conventional techniques and apparatus commonly used in molecular biology, microbiology, protein purification, protein engineering, protein and DNA sequencing, and recombinant DNA fields that are within the skill of the art. Such techniques and apparatus are known to those of skill in the art and are described in numerous texts and reference works (See e.g., Sambrook et al., "Molecular Cloning: A Laboratory Manual," Third Edition (Cold Spring Harbor), [2001]).

Numeric ranges are inclusive of the numbers defining the range. It is intended that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

The headings provided herein are not intended to limit the disclosure.

Unless defined otherwise herein, all technical and scientific terms used herein have the same meaning as commonly understood by one of ordinary skill in the art. Various scientific dictionaries that include the terms included herein are well known and available to those in the art. Although any methods and materials similar or equivalent to those described herein find use in the practice or testing of the embodiments disclosed herein, some methods and materials are described.

The terms defined immediately below are more fully described by reference to the Specification as a whole. It is to be understood that this disclosure is not limited to the particular methodology, protocols, and reagents described, as these may vary, depending upon the context they are used by those of skill in the art.

Definitions

As used herein, the singular terms "a," "an," and "the" include the plural reference unless the context clearly indicates otherwise.

Unless otherwise indicated, nucleic acids are written left to right in 5' to 3' orientation and amino acid sequences are written left to right in amino to carboxy orientation, respectively. The terms "polynucleotide," "nucleic acid" and "nucleic acid molecules" are used interchangeably and refer to a covalently linked sequence of nucleotides (i.e., ribonucleotides for RNA and deoxyribonucleotides for DNA) in which the 3' position of the pentose of one nucleotide is joined by a phosphodiester group to the 5' position of the pentose of the next. The nucleotides include sequences of any form of nucleic acid, including, but not limited to RNA and DNA molecules such as cell-free DNA (cfDNA) molecules. The term "polynucleotide" includes, without limitation, single- and double-stranded polynucleotides.

Amplified DNA sequence: A DNA sequence created by a polymerase chain reaction. The term first amplified nucleotide sequence refers to the amplification resulting from a first set of primers, and includes any subsequent amplification thereof, and the term a second amplified nucleotide sequence refers to the amplification resulting from a second set of primers, and includes any subsequent amplification thereof.

CRISPR: A method of nucleotide editing, insertion or deletion that utilizes the binding specification of specific enzymes (such as CAS) that recognize and cleave specific strands of DNA that are complementary to the CRISPR sequence.

Directional sequencing: refers to the sequencing in a specific direction, such as in a 5' to 3' direction or a 3' to 5' direction, depending upon the context used.

Genome: The entirety of the chromosomal information of a plant, animal or microbe contained in its DNA and RNA.

Hybridization fragment: a fragment of DNA or RNA of variable length that is complementary or substantially complementary with the sequence to which it will bind under normal hybridization conditions. The end of the PCR primer strand will comprise a hybridization fragment that will bind to the targeted nucleotide region of interest.

Linker: a short, chemically synthesized oligonucleotide that can be ligated to the ends of other DNA or RNA molecules. Double stranded adapters can be synthesized to have blunt ends to both terminals or to have sticky end at one end and blunt end at the other. For instance, a double stranded DNA adapter can be used to link the ends of two other DNA molecules (i.e., ends that do not have "sticky ends", that is complementary protruding single strands by themselves). Two adapters could base pair to each other to form dimers. If a second round of PCR is desired, linker sequences can be used to attach a third PCR primer strand and fourth PCR primer strand to linker sequences at the ends of the amplicon, which linker sequences may be initially placed there via the first PCR primer strand and the second PCR primer strand.

Massive parallel sequencing, also called next generation sequencing, NGS or next gen sequencing: Any one of several high throughput approaches to DNA sequencing. These technologies typically use miniaturized and parallelized platforms for sequencing millions to billions of short reads (50-400 bases each) per instrument run. These sequencing methods allow for massively parallel sequencing of clonally amplified molecules and of single nucleic acid molecules. Non-limiting examples of NGS include sequencing-by-synthesis using reversible dye terminators, and sequencing-by-ligation.

PCR, also called polymerase chain reaction: A repeated denaturization, annealing and elongation process that results in the amplification of a nucleotide sequence between two polymerase primers, one of which may be referred to as the forward primer, and the other as the reverse primer.

PCR primer strand: A nucleotide sequence comprising a PCR primer and other desired nucleotide sequences, such as a TUMI, a sample index, etc.

Polynucleotide length: Refers to the absolute number of nucleic acid molecules (nucleotides) in a sequence, fragment or strand of nucleotides.

Primer: Refers to an isolated oligonucleotide that is capable of acting as a point of initiation of synthesis when placed under conditions inductive to synthesis of an extension product (e.g., the conditions include nucleotides, an inducing agent such as DNA polymerase, necessary ions and molecules, and a suitable temperature and pH). The primer may be single stranded or double stranded. The primer may be an oligodeoxyribonucleotide. The primer is sufficiently long to prime the synthesis of extension products in the presence of the inducing agent. The exact lengths of the primers will depend on many factors, including temperature, source of primer, use of the method, and the parameters used for primer design.

Read: Refers to a sequence determined from a portion of a nucleic acid sample. Typically, though not necessarily, a read represents a short sequence of contiguous base pairs in the sample. The read may be represented symbolically by the base pair sequence in A, T, C, and G of the sample portion, together with a probabilistic estimate of the correctness of the base (quality score). It may be stored in a memory device and processed as appropriate to determine whether it matches a reference sequence or meets other criteria. A read may be obtained directly from a sequencing apparatus or indirectly from stored sequence information concerning the sample. In some cases, a read is a DNA sequence of sufficient length (e.g., at least about 20 bp) that can be used to identify a larger sequence or region, e.g., that can be aligned and mapped to a chromosome or genomic region or gene.

Sample index: A short sequence of DNA or RNA, typically 6-10 bases, that is specific to a given sample library and is used for de-multiplexing during data analysis to assign individual sequence reads to the correct sample. Sample indexes (or indices) enable multiple samples to be sequenced together (i.e., multiplexed) on the same instrument flow cell or chip. Adapters may contain single or dual sample indexes depending on the number of libraries combined and the level of accuracy desired.

Sequencing adaptor: A short piece of DNA of known sequence that is added to the ends of unknown DNA of interest, typically in order to place a sequencing primer at that location. Sequencing adapters may include platform-specific sequences for fragment recognition by the sequencer, and are used in massive parallel sequencing.

Sequencing primer: A short piece of DNA of known sequence that is used to initiate the sequencing reaction. The orientation of the sequencing primer (whether 5' to 3' or 3' to 5') will determine the direction of the sequencing reaction.

Sequencing primer binding site: A nucleotide region on the template DNA which is complementary to a specific sequencing primer so that the sequencing primer can bind and initiate the sequencing reaction.

Target Nucleotide Region of Interest: A sequence of nucleotides that has been modified or inserted into a genome by molecular biology techniques such as transformation, CRISPR, a zinc finger nuclease, FLP/FRT or other site specific recombination technology. The target nucleotide region of interest detected by the claimed method or system may be the DNA or RNA sequence representing the target nucleotide region of interest.

Transformation: A scientific approach whereby DNA from any organism is inserted into the genome of a species of interest. The inserted DNA is called a "transgene", and the resulting plant is said to be "transgenic". A transgenic event is a change in the DNA of the genome that is inserted into the genome in a particular chromosomal location.

Modified DNA: DNA that is inserted into a genome by transformation, or genomic DNA that has been modified by gene editing techniques, such as CRISPR/CAS.

INTRODUCTION

NGS methods are performed in a massively parallel fashion, affording increasingly high speed for determining biomolecules sequence information. However, many of the NGS methods and associated sample manipulation techniques introduce errors such that the resulting sequences have relatively high error rate, ranging from one error in a few hundred base pairs to one error in a few thousand base pairs. Such error rates are unacceptable for determining the identity of a target nucleotide region of interest (such as a transgenic event) because sequencing errors can cause false positives or negatives that are undesirable for scientific and regulatory reasons. Therefore, accuracy of measurement is paramount when reading plant nucleotides to determine the presence or absence of a transgenic event. By utilizing unique molecular indices as described herein, the benefit of the high speed and throughput of NGS sequencing can be utilized with a higher degree of accuracy than would be obtained via a direct read of the target nucleotide sequence of interest, such as a transgenic event.

TUMI

Unique molecular indices are sequences of nucleotides applied to or identified in DNA molecules that may be used to distinguish individual DNA molecules from one another. Since unique molecular indices are used to identify DNA molecules, they are also referred to as unique molecular identifiers. See, e.g., Kivioja, Nature Methods 9, 72-74 (2012). Unique molecular indices are typically sequenced along with the DNA molecules with which they are associated, for example, to determine whether the read sequences are those of one source DNA molecule or another.

The term "TUMI" is used herein to refer to both the sequence information of a polynucleotide and the physical polynucleotide per se. In particular, TUMI refers to a unique molecular sequence used to identify a particular transgenic event, although it also may be used to identify any nucleotide of interest located in a plant genome.

The TUMI sequence may be randomly generated or nonrandom. In most embodiments, it will be desirable for every TUMI sequence to differ from every other TUMI by a specified number of nucleotides. In some embodiments, all TUMI sequences will differ from every other TUMI sequence by at least two nucleotides, by at least three nucleotides, by at least four nucleotides, by at least five nucleotides, or by more than five nucleotides. In some embodiments, these differences are at corresponding sequence positions of each of the TUMI sequences.

In some implementations of the methods above, the TUMI sequence includes fewer than 20 nucleotides. In some implementations, the TUMI sequence includes fewer than 15 nucleotides. In some implementations, the TUMI sequence includes fewer than 10 nucleotides. In one embodiment tested, a TUMI sequence of eight nucleotides was successfully used.

In some embodiments, the TUMI has a sufficient length to ensure uniqueness for each and every source DNA molecule. In one embodiment tested, a TUMI of 26 nucleotides in length was used for detection, and each TUMI was unique from every other TUMI by at least 8 bases (a hamming distance of 8). A TUMI of 8 nucleotides in length was also tested, with each TUMI being unique from every other TUMI by at least 4 bases (a hamming distance of 4). In some implementations, a less unique molecular identifier can be used in conjunction with other identification techniques to ensure that each source DNA molecule is uniquely identified during the sequencing process. In such implementations, multiple fragments or adapters may be utilized with the TUMI to uniquely identify reads.

The TUMI method has application in several areas within the plant sciences, including but not limited to breeding applications, such as trait introgression, seed production trait purity testing, forward breeding trait identification and native trait detection.

Directional Sequencing

A sequencing primer binding site, which serves as the initiating point of the sequencing reaction, is positioned between the TUMI sequence and the target nucleotide region of interest on the amplicon to be sequenced. The sequencing primer, with correct orientation to the sequencing primer binding site, will initiate sequencing in the direction of the TUMI sequence. Since it is directional, the target nucleotide region of interest is not sequenced.

In some embodiments, it may be beneficial to place a second sequencing primer at the other end of the amplicon, also positioned to initiate the sequence away from the targeted nucleotide region of interest.

Target Nucleotide Region of Interest

The target nucleotide region of interest is a sequence of nucleotides in the plant genome that has been modified or inserted into the plant genome by molecular biology techniques such as transformation, CRISPR, a zinc finger nuclease, FLP/FRT or other site specific recombination technology.

Examples of target nucleotide regions of interest include stably incorporated transgene sequences, native trait sequences and allelic variants thereof. Other target nucleotide regions of interest include any non-coding or coding sequences with the function of interests in the genome. In various embodiments of this invention, the target nucleotide regions of interest are transgenic events of maize, transgenic events of soybean, transgenic events of canola, transgenic events of wheat, or transgenic events of rice. Other targeted nucleotide sequences of interest include native traits or CRISPR modified traits, such as the white or waxy trait of corn. Targeted nucleotides of interest may also be conserved non-coding sequences or regulatory elements such as promoters, enhancers or other protein binding sides.

Some examples of target nucleotide regions of interest that may be detected using the methods described herein include, but are not limited to:

| Trait | Crop | Event |
|---|---|---|
| Abiotic Stress Tolerance | Maize (*Zea mays L.*) | MON87460 |
| Abiotic Stress Tolerance | Soybean (*Glycine max L.*) | HB4 |
| Abiotic Stress Tolerance | Sugarcane (*Saccharum* sp.) | NXI-1T, NXI-4T, NXI-6T |
| Altered Growth/Yield | Eucalyptus (*Eucalyptus* sp.) | H421 |
| Altered Growth/Yield | Maize (*Zea mays L.*) | MON87403 |
| Altered Growth/Yield | Soybean (*Glycine max L.*) | MON87712 |
| Disease Resistance | Bean (*Phaseolus vulgaris*) | EMBRAPA 5.1 |
| Disease Resistance | Papaya (*Carica papaya*) | 55-1, 63-1, Huanong No. 1, X17-2 |
| Disease Resistance | Plum (*Prunus domestica*) | C-5 |
| Disease Resistance | Potato (*Solanum tuberosum L.*) | HLMT15-15, HLMT15-3, HLMT15-46, RBMT15-101, RMT21-129, RBMT21-152, RBMT21-350, RBMT22-082, RBMT22-186, RBMT22-238, RBMT22-262, SEMT15-02, SEMT15-07, SEMT15-15, SP951, TIC-AR233-5, W8, X17, Y9 |
| Disease Resistance | Squash (*Cucurbita pepo*) | CZW3, ZW20 |
| Herbicide Tolerance | Alfalfa (*Medicago sativa*) | J101, J163 |
| Herbicide Tolerance | Canola (*Brassica napus*) | 61061, 73496, GT200, GT73, HCN10, HCN28, MON88302, HCN92, MS8, MS1, OXY-235, PHY14, PHY23, PHY35, PHY36, RF3 |
| Herbicide Tolerance | Cotton (*Gossypium hirsutum L.*) | 19-51a, 281-24-236, 3006-210-23, 81910, MON1445, MON88913, 31707, 31803, 31807, 31808, 42317, BXN10211, BXN10215, BXN10222, BXN10224, COT67B, MON15895, MON88701, GHB119, GHB614, LLCotton25, T304-40, GHB811, MON1698, MON531, MON88701, T303-3, GHB119 |
| Herbicide Tolerance | Creeping Bentgrass (*Agrostis stolonifera*) | ASR368 |
| Herbicide Tolerance | Maize (*Zea mays L.*) | 3272, Bt11, 59122, MIR604, TC1507, GA21, 5307, 33121, 4114, MIR162, DAS40278, MON810, NK603, MON88017, 676, 678, 680, 98140, Bt10, MON89034, Bt176, CBH-351, DBT418, DLL25, HCEM485, MON87411, MON87419, MON87427, MON87460, MZHG0JG, MZIR098, T25, T14, TC6275, VCO-01981-5 |
| Herbicide Tolerance | Potato (*Solanum tuberosum L.*) | RBMT22-082, RBMT22-186, RBMT22-238, RBMT22-262 |
| Herbicide Tolerance | Rice (*Oryza sativa L.*) | LLRICE06, LLRICE601, LLRICE62 |
| Herbicide Tolerance | Soybean (*Glycine max L.*) | A27014-12, A2704-21, A5547-127, A5547-35, CV127, DAS44406-6, DAS68416-4, MON89788, DP305423, GTS40-3-2, MON88708, DP356043, FG72, A5547-127, GU262, HB4, MON87701, MON87705, MON89788, MON87751, MON87769, SYHT0H2, W62, W98 |
| Herbicide Tolerance | Sugar Beet (*Beta vulgaris*) | GTSB77, H7-1, T120-7 |
| Herbicide Tolerance | Wheat (*Triticum aestivum*) | MON71800 |
| Insect Resistance | Cotton (*Gossypium hirsutum L.*) | 281-24-236, 3006-210-23, COT102, 81910, 31803, 31807, 31808, 42317, BNLA-601, MON1445, COT67B, JK1, GK12, MON1076, MON15985, |

-continued

| Trait | Crop | Event |
|---|---|---|
| Insect Resistance | Maize (*Zea mays L.*) | MON531, MON757, MON88702, SGK321, T303-3, GHB119 Bt11, 59122, TC1507, MIR604, DP33121, DP4114, 5307, MON810, MON88017, MIR162, MON89034, MON87411, MZIR098, |
| Insect Resistance | Potato (*Solanum tuberosum L.*) | 1210amk, 2904/1 kgs, ATBT04-27, ATBT04-30, ATBT04-31, ATBT04-36, ATBT04-6, BT06, BT10, BT12, BT16, BT17, BT18, BT23, HLMT15-15, HLMT15-3, HLMT15-46, RBMT15-101, RBMT21-29, RBMT21-152, RBMT21-129, RBMT21-350, RBMT22-082, RBMT22-186, RBMT22-238, RBMT22-262, SEMT15-02, SEMT15-07, SEMT15-15, SPBT02-5, SPBT02-7 |
| Insect Resistance | Rice (*Oryza sativa L.*) | GM Shanyou 63, Huahui 1/TT51-1 |
| Insect Resistance | Soybean (*Glycine max L.*) | DAS81419, MON87701, MON87751, |
| Insect Resistance | Sugarcane (*Saccharum* sp.) | CTC175-A, CTC91087-6 |
| Modified Product Quality | Alfalfa (*Medicago sativa*) | KK179 |
| Modified Product Quality | Apple (*Malus × domestica*) | GD743, GS784, NF872 |
| Modified Product Quality | Carnation (*Dianthus caryophyllus*) | 11, 11363, 1226A, 123.2.2, 123.2.38, 123.8.12, 123.8.8, 1351A, 1400A, 15, 16, 19907, 25947, 25958, 26407, 4, 66, 949A, 988A |
| Modified Product Quality | Maize (*Zea mays L.*) | 3272, LY038 |
| Modified Product Quality | Potato (*Solanum tuberosum L.*) | AM04-1020, E12, E24, E56, EH92-527-1, F10, F37, G11, H37, H50, J3, J55, J78, V11, W8, X17, Y9 |
| Modified Product Quality | Soybean (*Glycine max L.*) | DP305423, MON87705 |
| Pollination Control System | Canola (*Brassica napus*) | RF1, RF2, RF3 |
| Pollination Control System | Maize (*Zea mays L.*) | DP32138, MS3, MS6 |

Sample Indices

Sample indices, sometimes referred to as sample bar codes, may be used in conjunction with the TUMI sequences. Sample indices are used to distinguish reads of one sample from reads of other samples, whereas TUMIs are instead used to identify a targeted nucleotide region of interest. A sample index is a short sequence of DNA or RNA, typically 6-10 bases, that is specific to a given sample library and is used for de-multiplexing during data analysis to assign individual sequence reads to the correct sample. Sample indexes (or indices) enable multiple samples to be sequenced together (i.e., multiplexed) on the same instrument flow cell or chip. Adapters may contain single or dual sample indexes depending on the number of libraries combined and the level of accuracy desired.

The sample index may be added in various ways. It may be added with a PCR primer as part of a PCR primer strand used in either the first or second or subsequent PCR. As with the TUMI, the sample index sequence has a sequencing primer in between the targeted nucleotide region of interest and the sample index which will direct sequencing in the direction of the sample index, so that the targeted nucleotide sequence of interest is not sequenced. The sample index may be in line for sequencing with the TUMI sequence, such as adjacent to the TUMI sequence, or may be in a short paired end at the other end of the amplicon sequenced.

The term "paired end reads" refers to reads obtained from paired end sequencing that obtains one read from each end of a nucleic fragment. Paired end sequencing involves fragmenting DNA into sequences called inserts. The reads from shorter inserts (e.g., on the order of tens to hundreds of bp) are referred to as short-insert paired end reads or simply paired end reads.

The methods and apparatus described herein may employ next generation sequencing technology (NGS), which allows massively parallel sequencing. In certain embodiments, clonally amplified DNA templates or single DNA molecules are sequenced in a massively parallel fashion within a flow cell (e.g., as described in Volkerding et al. Clin Chem 55:641-658 [2009]; Metzker M Nature Rev 11:31-46 [2010]).

The sequencing technologies of NGS include but are not limited to pyrosequencing, sequencing-by-synthesis with reversible dye terminators, sequencing by oligonucleotide probe ligation, and ion semiconductor sequencing. DNA from individual samples can be sequenced individually (i.e., singleplex sequencing) or DNA from multiple samples can be pooled and sequenced as indexed genomic molecules (i.e., multiplex sequencing) on a single sequencing run, to generate up to several hundred million reads of DNA sequences. Examples of sequencing technologies that can be used to obtain the sequence information according to the present method are further described here. Once sequenced, the TUMI sequences are read and associated with the sample. Since each TUMI is unique to a specific targeted nucleotide sequence of interest, such as a transgene, the read may be used to automatically determine the transgenic events present or absent in the sample.

Dimer Cleanup

In some embodiments of the method, a dimer clean-up step may be added to improve the accuracy of the result. Dimers of primer may form during PCR when primer molecules have hybridized with each other because of strings of complementary bases in the primers. These dimers interfere with the PCR reaction and/or quantification in quantitative PCR. Designing different primers to avoid primer dimer formation may not be a viable option and using hot start PCR may not be sufficient. Thus, in some embodiments of the method there is a dimer clean-up step that may be introduced between the first and second PCR rounds. This clean-up step may be accomplished via bead based purification, gel based size selection, size selection bead matrix, or silica membrane purification.

Quantitative PCR

The method described herein may be utilized with either qualitative PCR or quantitative PCR. Quantitative PCR may be performed by utilizing one or more normalizer genes or sequences with a known copy number in the genome, together with randomized unique molecular ID's incorporated in the PCR primers in the first PCR cycle. This allows for quantification of the amount of a specific nucleotide region of interest in the sample relative to the normalizer genes or sequences. The data may then be de-duplicated to account for only the amplification products that represent a unique primer annealing event.

Genome Wide Marker Analysis

The targeted unique molecular index may be used in combination with genome wide molecular markers in one sample processing step. This is useful for improving the efficiency of plant breeding. For example, molecular marker assisted backcross breeding, used to more efficiently introgress transgenic trait events into the genome of elite germplasm lines, may be used in combination with TUMI to enhance the transfer of one or more transgenic trait events while maintaining as much of the genome of elite germplasm line as possible. Genomic markers are used to minimize the amount of the donor genome (other than the transgenic trait event) is transferred into the elite germplasm line. TUMI is used to detect the event locus of interest, without sequencing it directly, while genome wide markers are used to detect the origin of the flanking and other genomic regions in order to achieve this objective. Both transgenic regions with TUMI and genome wide markers are captured, enriched and then TUMI and genomic region amplicon are sequenced simultaneously in the same Next-Generation Sequencing (NGS) reaction, and the TUMI sequences from amplicons from transgenic regions and the marker sequences from amplicons from genomic regions are then sequenced. The analysis of sequencing data is performed so that transgene events (using TUMI technology) and genomic targets (using SNPs or other markers) may be called at the same time.

Figure 5:
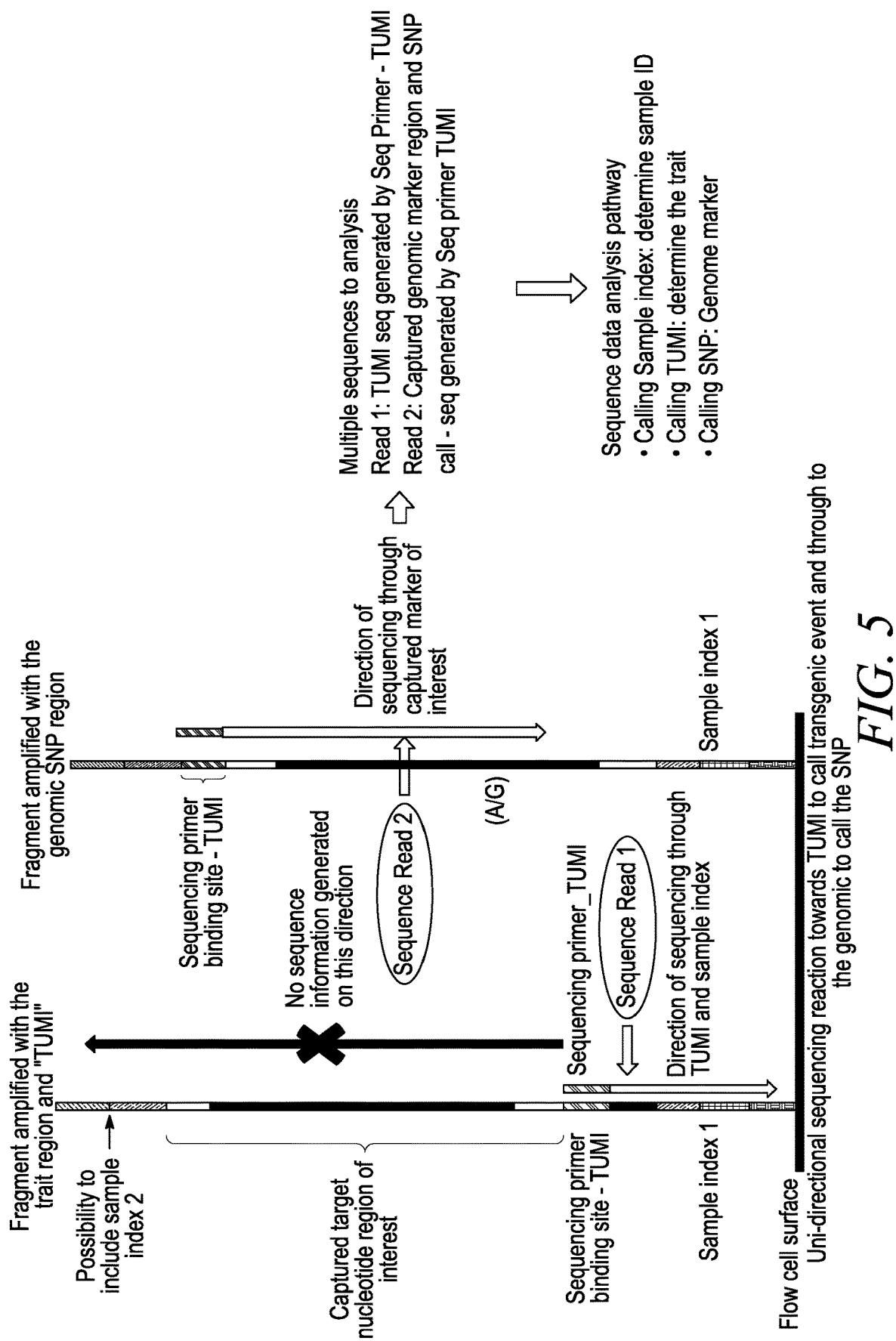
FIG. 5 Schematic diagram of the TUMI reaction used in combination with genome wide markers showing the direction of sequencing.

In this embodiment, the TUMI sequences are used in combination with the genome wide markers, such as single nucleotide polymorphisms or haplotypes of single nucleotide polymorphisms located throughout the genome. Library preparation employs both types of these sequences (e.g. TUMI and SNP sequences) and genomic regions are captured and enriched by incorporating the same sequencing primer site utilized in the TUMI based amplicon. As described in FIG. 5, the same sequencing primer binding site used in the TUMI amplicon to sequence through the sample index and away from the target nucleotide region of interest is positioned proximal to the genomic marker region such that the sequence of the genomic marker (e.g. the SNP call) will be sequenced and determined in the same reaction as the TUMI based determination. Thus, the identity of the trait locus and the genomic marker information may be identified in the same sequencing reaction.

When TUMI sequences are used in combination with genome wide markers, the genomic marker sequencing library is prepared by incorporating a sequencing primer site that is the same sequencing primer site used in the TUMI amplicon, or at least similar enough to cause the sequencing primer to bind proximal to the genomic marker region so that such region is sequenced during the multiplex. A sample index may then be added, as well as any NGS specific adapters needed for sequencing. These additions may be achieved by PCR amplification (such as in a second round reaction), by capturing the targets with adapter ligation, or by other techniques known in the art, but in each case the TUMI sequencing primer binding site common to TUMI is positioned such that sequencing will read through the genomic marker region. This is contrast to the use of the TUMI sequencing primer proximal to the target nucleotide region of interest, where the sample index is sequenced without sequencing the target nucleotide region of interest. Resulting PCR products from multiple samples are pooled and purified to remove free primers and nucleotides, leaving the targeted amplicons at a desirable length for sequencing. The PCR reaction and assay conditions may be optimized via primer titration, thermal cycling parameters, PCR product size selection for the first round of PCR, purification and manipulating TUMI length, and purification of the NGS sequencing pool. Sequencing reads are deconvoluted to aggregate all reads from a single sample. These reads may then be quality trimmed to exclude any poor quality base reads. A FASTQ file for each sample may then be binned using TUMI to count all unique TUMI sequences present within a given sample. The relative abundance of each TUMI sequence will be determined on a per sample basis and used as the basis for calling presence/absence of the corresponding DNA associated with that TUMI.

EXAMPLES

TUMI

Figure 2:
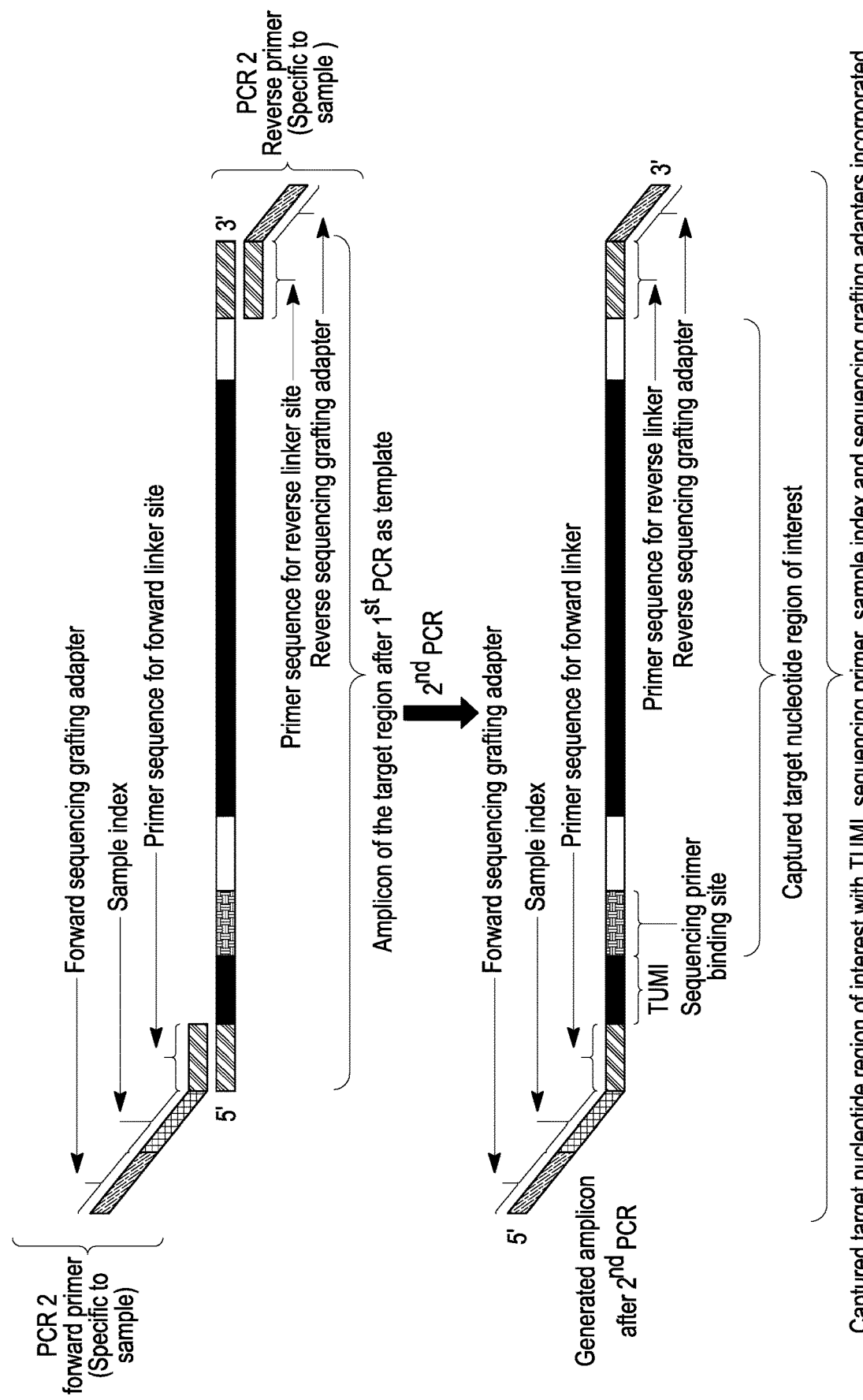
FIG. 2 Schematic diagram of the generation of an amplicon from a second PCR reaction that places a sample index and grafting adapters on the amplicon generated from the first PCR reaction.
Figure 3:
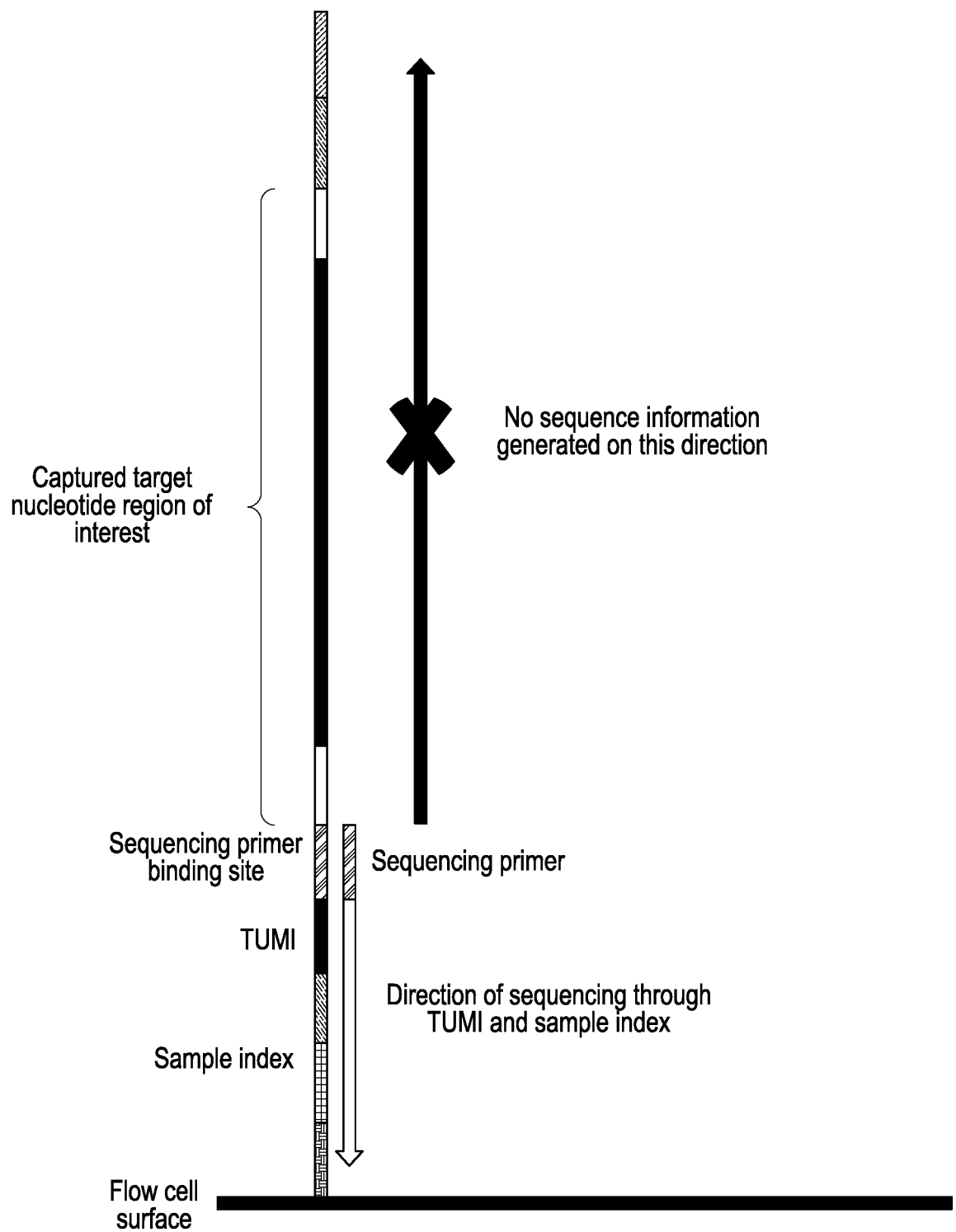
FIG. 3 Schematic diagram of the sequencing reaction that sequences in the direction of the TUMI sequence and does not sequence the targeted nucleotide region of interest.

Maize genomic DNA comprising a transgenic event was extracted. In this experiment, three sample groups were run, one with a maize variety event comprising event DAS01507 (TC1507), one with a maize variety comprising event DAS59122 and one with a maize variety event containing event DAS40278. More information about TC1507, DAS59122 and DAS40278 may be obtained online from the International Service for the Acquisition of Agri-Biotech Applications, c/o IP CALs, B75 Mann Library Cornell University, Ithaca, New York 14853, USA, at www.isaaa.org. Sequencing libraries were prepared by using a two-step PCR process illustrated and described in FIGS. 1-2. The first PCR step incorporated a) event specific primers that target these transgenic events, b) unique TUMI sequences, in this embodiment designed to specifically identify each of TC1507, DAS59122 and DAS40278, with each TUMI sequence being 26 nucleotides in length and having a hamming distance of at least 8 nucleotides from any other TUMI sequence, c) sequencing primers directing sequencing towards TUMI and away from the transgenic target regions, and d) linker sequences to bind primers for the second PCR step. The second PCR step further incorporated a) the sample index and b) sequencing grafting adapters to the DNA template (amplicon) obtained as the product of the first PCR step. Multiple PCR products from the two step PCR process were run through agarose gel electrophoresis and the size of the amplicons were confirmed, with the size of each amplicon being the expected number of base pair larger than the original target region. The orientation of the various components illustrated in FIGS. 1-2 can be altered, for example the forward and reverse primer pairs can be switched in 5' to 3' orientation, so long as the directional sequencing occurs in a direction that includes the TUMI sequence and does not include the nucleotide region of interest, such as in the manner illustrated in FIG. 3.

The TC1507 TUMI results are illustrative of the accuracy of the method. Following the first PCR step, a custom sequencing primer binding site was positioned immediately adjacent to the 3' end of the TUMI sequence, with the direction of the sequencing primer causing the TUMI sequence to be read without obtaining any transgene sequence in 34,163 sequencing reads. The pooled amplicon products were run on an Illumina MiSeq system, with a single read 50 cycle sequence followed by an indexing read for sample deconvolution. Out of 34,163 total reads for the TUMI sequence specific to TC1507, 32,650 reads were a perfect match for the TUMI sequence. The remaining 1,513 reads were single mismatch reads, easily identified to the TUMI sequence for TC1507 as a result of using a Hamming Distance of 8 between all TUMI sequences used. Therefore, the TUMI sequences accurately identified the event with which they were associated 100% of the time.

Multiplexed TUMI assays were also tested. Each sample assay included event 59122, adh2 (alcohol dehydrogenase) as a control, -DAS40278- and TC1507. TUMI barcodes correctly identified any or all of the 4 types of events/genes present in each sample.

TUMI in Combination with Genome Wide Markers

In this experiment, maize genomic DNA comprising the transgenic event(s) were extracted. Five sample groups were run, one with a maize variety event comprising event DAS01507 (TC1507), one with a maize variety comprising event DAS59122 and one with a maize variety event containing event DAS40278, a hybrid control sample (SX19) and non-maize DNA (Soy) as a blank sample. All transgenic maize samples contain the expected trait target(s) and two genomic SNP locus targets. Sequencing libraries were prepared by using the two-step PCR process described herein.

The first PCR step incorporated two types of targets, a trait and a SNP locus. The trait target comprised of: a) event specific primers that target the transgenic events b) the unique TUMI sequences designed to specifically identify each of TC1507, DAS59122 and DAS40278, with each TUMI sequence being 26 nucleotides in length and having a hamming distance of at least 8 nucleotides from any other TUMI sequence, c) sequencing primers directing sequencing towards TUMI and away from the transgenic target regions, and d) linker sequences to bind primers for the second PCR step. The genomic SNP locus targets comprised: a) SNP assay primers that amplify the region containing the SNP locus. b) sequencing primers utilized same design as the TUMI sequencing primer with its orientation to direct the single end NGS sequencing reaction towards the target genomic region to ensure the final amplified fragment will sequence through the captured genomic fragment, and c) linker sequences to bind primers for the second PCR step. These two types of target primers were multiplexed in order to capture both traits and genomic regions in one reaction.

Several iterations of cycling conditions and assay concentrations were tested during an optimization phase of the first PCR. The final assay concentration for the trait and genomic assays were set to be 200 nM. The PCR cycle number for the first PCR step was set to 30 after testing 20, 30 and 40 cycle numbers showed 30 cycles yielded the best results in terms of reduction of unexpected amplification such as primer dimmers in the PCR product.

Figure 6:
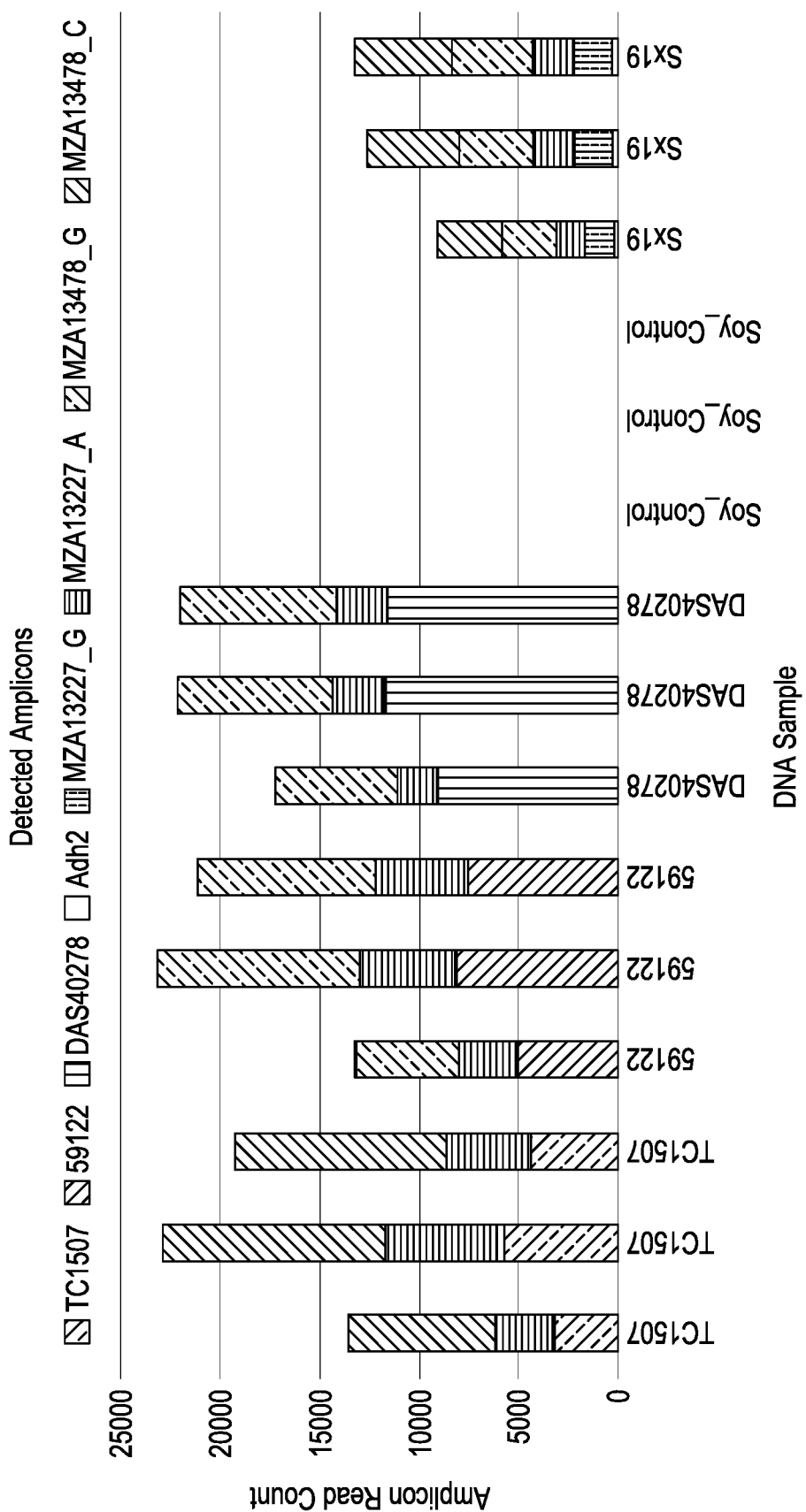
FIG. 6 Shows the analysis of sequencing reads of the pooled amplicon library, generated using two step PCR, demonstrating correct detection of transgenic traits and corresponding genomic SNP targets with respective allele calls.

The second PCR step incorporated a) the sample index and b) sequencing grafting adapters to the DNA template (amplicon) to the product of the first PCR step. The pooled amplicon products were purified and run on an Illumina MiSeq system, with a single read 50 cycle sequence followed by an indexing read for sample deconvolution. Out of 34,163 total reads for the TUMI sequence specific to TC1507, 32,650 reads were a perfect match for the TUMI sequence. The remaining 1,513 reads were single mismatch reads, easily identified to the TUMI sequence for TC1507 as a result of using a Hamming Distance of 8 between all TUMI sequences used. Therefore, the TUMI sequences accurately identified the event with which they were associated. Multiplexed TUMI assays were also tested. Each sample assay included all three transgenic events (59122, DAS40278, TC1507), adh2 (alcohol dehydrogenase) as an endogenous control gene target, and two internal genomic SNP locus assays (MZA13478 and MZA13227). TUMI barcodes correctly identified any or all of the 4 types of events/genes present in each sample. For genomic target regions, the use of sequencing primer (same design as TUMI sequencing primer) enable multiplexing with trait TUMI detection. The genomic target region sequence amplicon determines the SNP allele type in the corresponding samples. Therefore, for every sample in this experiment, the trait's present/absent status and a SNP allele type for every genomic targets included in the multiplexing assays was correctly determined (FIG. 6).

Sequencing Technologies

Some sequencing technologies are available commercially, such as the sequencing-by-hybridization platform from Affymetrix Inc. (Sunnyvale, Calif.) and the sequencing-by-synthesis platforms from 454 Life Sciences (Bradford, Conn.), Illumina/Solexa (Hayward, Calif.) and Helicos Biosciences (Cambridge, Mass.), and the sequencing-by-ligation platform from Applied Biosystems (Foster City, Calif.), as described below. In addition to the single molecule sequencing performed using sequencing-by-synthesis of Helicos Biosciences, other single molecule sequencing technologies include, but are not limited to, the SMRT.TM. technology of Pacific Biosciences, the ION TORRENT.TM. technology, and nanopore sequencing developed for example, by Oxford Nanopore Technologies.

While the automated Sanger method is considered as a 'first generation' technology, Sanger sequencing including the automated Sanger sequencing, can also be employed in the methods described herein. Additional suitable sequencing methods include, but are not limited to nucleic acid imaging technologies, e.g., atomic force microscopy (AFM) or transmission electron microscopy (TEM).

In some embodiments, the disclosed methods involve obtaining sequence information for the nucleic acids in the test sample by massively parallel sequencing. Template DNA can be genomic DNA, e.g., cellular DNA. In some embodiments, genomic DNA from isolated cells is used as the template, and it is fragmented into lengths of several hundred base pairs.

DNA is prepared for sequencing by adding grafting adapters, which may have an overhang of a single T base at their 3' end to increase ligation efficiency. The adapter oligonucleotides are complementary to the flow-cell anchor oligos. Under limiting-dilution conditions, adapter-modified, single-stranded template DNA is added to the flow cell and immobilized by hybridization to the anchor oligos. Attached DNA fragments are extended and bridge amplified to create an ultra-high density sequencing flow cell with hundreds of millions of clusters, each containing about 1,000 copies of the same template.

In some applications, the templates are sequenced using a robust one-color, two-color or four-color DNA sequencing-by-synthesis technology that employs reversible terminators with removable fluorescent dyes. High-sensitivity fluorescence detection is achieved using laser excitation and total internal reflection optics. Short sequence reads of about tens to a few hundred base pairs may be aligned against a reference set of DNA, TUMI or genome sequences and identification or mapping are identified using data analysis software. After completion of the first read, the templates can be regenerated in situ to enable a second read from the opposite end of the fragments. Thus, either single-end or paired end sequencing of the DNA fragments can be used.

Various embodiments of the disclosure may use sequencing by synthesis that allows paired end sequencing. In some embodiments, the sequencing by synthesis platform by Illumina involves clustering fragments. Clustering is a process in which each fragment molecule is isothermally amplified. In some embodiments, as the example described here, the fragment has two different adapters attached to the two ends of the fragment, the adapters allowing the fragment to hybridize with the two different oligos on the surface of a flow cell lane. The fragment further includes or is connected to two index sequences at two ends of the fragment, which index sequences provide labels to identify different samples in multiplex sequencing.

In some implementation, a flow cell for clustering, such as a glass slide with lanes, is used. Each lane is a glass channel coated with a lawn of two types of oligos (e.g., P5 and P7' oligos). Hybridization is enabled by the first of the two types of oligos on the surface. This oligo is complementary to a first adapter on one end of the fragment. A polymerase creates a compliment strand of the hybridized fragment. The double-stranded molecule is denatured, and the original template strand is washed away. The remaining strand, in parallel with many other remaining strands, is clonally amplified through bridge application.

In bridge amplification and other sequencing methods involving clustering, a strand folds over, and a second adapter region on a second end of the strand hybridizes with the second type of oligos on the flow cell surface. A polymerase generates a complementary strand, forming a double-stranded bridge molecule. This double-stranded molecule is denatured resulting in two single-stranded molecules tethered to the flow cell through two different oligos. The process is then repeated over and over, and occurs simultaneously for millions of clusters resulting in clonal amplification of all the fragments. After bridge amplification, the reverse strands are cleaved and washed off, leaving only the forward strands. The 3' ends are blocked to prevent unwanted priming.

After clustering, sequencing starts with extending a first sequencing primer to generate the first read. In this method, the sequencing primer directs the sequencing to TUMI and away from the targeted regions of interests. With each cycle, fluorescently tagged nucleotides compete for addition to the growing chain. Only one is incorporated based on the sequence of the template. After the addition of each nucleotide, the cluster is excited by a light source, and a characteristic fluorescent signal is emitted. The number of cycles determines the length of the read. The emission wavelength and the signal intensity determine the base call. For a given cluster all identical strands are read simultaneously. Hundreds of millions of clusters are sequenced in a massively parallel manner. At the completion of the first read, the read product is washed away.

In the next step of protocols involving two index primers, an index 1 primer is introduced and hybridized to an index 1 region on the template. Index regions provide identification of fragments, which is useful for de-multiplexing samples in a multiplex sequencing process. The index 1 read is generated similar to the first read. After completion of the index 1 read, the read product is washed away and the 3' end of the strand is de-protected. The template strand then folds over and binds to a second oligo on the flow cell. An index 2 sequence is read in the same manner as index 1. Then an index 2 read product is washed off at the completion of the step.

After reading two indices, read 2 initiates by using polymerases to extend the second flow cell oligos, forming a double-stranded bridge. This double-stranded DNA is denatured, and the 3' end is blocked. The original forward strand is cleaved off and washed away, leaving the reverse strand. Read 2 begins with the introduction of a read 2 sequencing primer. As with read 1, the sequencing steps are repeated until the desired length is achieved. The read 2 product is washed away. This entire process generates millions of reads, representing all the fragments. Sequences from pooled sample libraries are separated based on the unique indices introduced during sample preparation. For each sample, reads of similar stretches of base calls are locally clustered. Forward and reversed reads are paired creating contiguous sequences. These contiguous sequences are aligned to the reference genome for variant identification.

The sequencing by synthesis example described above involves paired end reads, which is used in some embodiments of the disclosed methods, such as when a pair of one directional primers are used that do not allow sequencing into the targeted nucleotide region of interest. Paired end sequencing involves 2 reads from the two ends of a fragment. Paired-end sequencing allows users to choose the length of the insert (or the fragment to be sequenced) and sequence either end of the insert. Paired-end sequencing can detect the TUMI and sample indices even when they are at opposite ends of the targeted nucleotide region of interest.

After sequencing of DNA fragments, sequence reads of predetermined length are identified. Since the TUMI sequences are predetermined, they can be compared with a database of all known TUMI sequences and used to identify the transgene or other targeted nucleotide region of interest. The sample indices can be similarly identified.

In one illustrative, but non-limiting, embodiment, the methods described herein include obtaining sequence information for the nucleic acids in a test sample, using single molecule sequencing technology of the Helicos True Single Molecule Sequencing (tSMS) technology (e.g. as described in Harris T. D. et al., Science 320:106-109 [2008]). In the tSMS technique, a DNA sample is cleaved into strands of approximately 100 to 200 nucleotides, and a polyA sequence is added to the 3' end of each DNA strand. Each strand is labeled by the addition of a fluorescently labeled adenosine nucleotide. The DNA strands are then hybridized to a flow cell, which contains millions of oligo-T capture sites that are immobilized to the flow cell surface. In certain embodiments the templates can be at a density of about 100 million templates/cm.sup.2. The flow cell is then loaded into an instrument, e.g., HeliScope.TM. sequencer, and a laser illuminates the surface of the flow cell, revealing the position of each template. A CCD camera can map the position of the templates on the flow cell surface. The template fluorescent label is then cleaved and washed away. The sequencing reaction begins by introducing a DNA polymerase and a fluorescently labeled nucleotide. The oligo-T nucleic acid serves as a primer, which can be positioned and oriented as described herein. The polymerase incorporates the labeled nucleotides to the primer in a template directed manner. The polymerase and unincorporated nucleotides are removed. The templates that have directed incorporation of the fluorescently labeled nucleotide are discerned by imaging the flow cell surface. After imaging, a cleavage step removes the fluorescent label, and the process is repeated with other fluorescently labeled nucleotides until the desired read length is achieved. Sequence information is collected with each nucleotide addition step.

In another illustrative, but non-limiting embodiment, the methods described herein include obtaining sequence information for the nucleic acids in the test sample, using the 454 sequencing (Roche) (e.g. as described in Margulies, M. et al. Nature 437:376-380 [2005]). 454 sequencing typically involves two steps. In the first step, DNA is sheared into fragments of approximately 300-800 base pairs, and the fragments are blunt-ended. Oligonucleotide adapters are then ligated to the ends of the fragments. The adapters serve as primers for amplification and sequencing of the fragments. The fragments can be attached to DNA capture beads, e.g., streptavidin-coated beads using, e.g., adapter B, which contains 5'-biotin tag. The fragments attached to the beads are PCR amplified within droplets of an oil-water emulsion. The result is multiple copies of clonally amplified DNA fragments on each bead. In the second step, the beads are captured in wells (e.g., picoliter-sized wells). Pyrosequencing is performed on each DNA fragment in parallel. Addition of one or more nucleotides generates a light signal that is recorded by a CCD camera in a sequencing instrument. The signal strength is proportional to the number of nucleotides incorporated. Pyrosequencing makes use of pyrophosphate (PPi) which is released upon nucleotide addition. PPi is converted to ATP by ATP sulfurylase in the presence of adenosine 5' phosphosulfate. Luciferase uses ATP to convert luciferin to oxyluciferin, and this reaction generates light that is measured and analyzed.

In another illustrative, but non-limiting embodiment, the methods described herein includes obtaining sequence information for the nucleic acids in the test sample, using the SOLiD.TM. technology (Applied Biosystems). In SOLiD.TM. sequencing-by-ligation, genomic DNA is sheared into fragments, and adapters are attached to the 5' and 3' ends of the fragments to generate a fragment library. Alternatively, internal adapters can be introduced by ligating adapters to the 5' and 3' ends of the fragments, circularizing the fragments, digesting the circularized fragment to generate an internal adapter, and attaching adapters to the 5' and 3' ends of the resulting fragments to generate a mate-paired library. Next, clonal bead populations are prepared in microreactors containing beads, primers, template, and PCR components. Following PCR, the templates are denatured and beads are enriched to separate the beads with extended templates. Templates on the selected beads are subjected to a 3' modification that permits bonding to a glass slide. The sequence can be determined by sequential hybridization and ligation of partially random oligonucleotides with a central determined base (or pair of bases) that is identified by a specific fluorophore. After a color is recorded, the ligated oligonucleotide is cleaved and removed and the process is then repeated.

In another illustrative, but non-limiting, embodiment, the methods described herein include obtaining sequence information for the nucleic acids in the test sample, using the single molecule, real-time (SMRT.TM.) sequencing technology of Pacific Biosciences. In SMRT sequencing, the continuous incorporation of dye-labeled nucleotides is imaged during DNA synthesis. Single DNA polymerase molecules are attached to the bottom surface of individual zero-mode wavelength detectors (ZMW detectors) that obtain sequence information while phospholinked nucleotides are being incorporated into the growing primer strand. A ZMW detector includes a confinement structure that enables observation of incorporation of a single nucleotide by DNA polymerase against a background of fluorescent nucleotides that rapidly diffuse in an out of the ZMW (e.g., in microseconds). It typically takes several milliseconds to incorporate a nucleotide into a growing strand. During this time, the fluorescent label is excited and produces a fluorescent signal, and the fluorescent tag is cleaved off. Measurement of the corresponding fluorescence of the dye indicates which base was incorporated. The process is repeated to provide a sequence.

In another illustrative, but non-limiting, embodiment, the methods described herein include obtaining sequence information for the nucleic acids in the test sample, using nanopore sequencing (e.g. as described in Soni G V and Meller A. Clin Chem 53: 1996-2001 [2007]). Nanopore sequencing DNA analysis techniques are developed by a number of companies, including, for example, Oxford Nanopore Technologies (Oxford, United Kingdom), Sequenom, NABsys, and the like. Nanopore sequencing is a single-molecule sequencing technology whereby a single molecule of DNA is sequenced directly as it passes through a nanopore. A nanopore is a small hole, typically of the order of 1 nanometer in diameter. Immersion of a nanopore in a conducting fluid and application of a potential (voltage) across it results in a slight electrical current due to conduction of ions through the nanopore. The amount of current that flows is sensitive to the size and shape of the nanopore. As a DNA molecule passes through a nanopore, each nucleotide on the DNA molecule obstructs the nanopore to a different degree, changing the magnitude of the current through the nanopore in different degrees. Thus, this change in the current as the DNA molecule passes through the nanopore provides a read of the DNA sequence.

In another illustrative, but non-limiting, embodiment, the methods described herein includes obtaining sequence information for the nucleic acids in the test sample, using the chemical-sensitive field effect transistor (chemFET) array (e.g., as described in U.S. Patent Application Publication No. 2009/0026082). In one example of this technique, DNA molecules can be placed into reaction chambers, and the template molecules can be hybridized to a sequencing primer bound to a polymerase. Incorporation of one or more triphosphates into a new nucleic acid strand at the 3' end of the sequencing primer can be discerned as a change in current by a chemFET. An array can have multiple chemFET sensors. In another example, single nucleic acids can be attached to beads, and the nucleic acids can be amplified on the bead, and the individual beads can be transferred to individual reaction chambers on a chemFET array, with each chamber having a chemFET sensor, and the nucleic acids can be sequenced.

In another embodiment, the DNA sequencing technology is the Ion Torrent single molecule sequencing, which pairs semiconductor technology with a simple sequencing chemistry to directly translate chemically encoded information (A, C, G, T) into digital information (0, 1) on a semiconductor chip. In nature, when a nucleotide is incorporated into a strand of DNA by a polymerase, a hydrogen ion is released as a byproduct. Ion Torrent uses a high-density array of micro-machined wells to perform this biochemical process in a massively parallel way. Each well holds a different DNA molecule. Beneath the wells is an ion-sensitive layer and beneath that an ion sensor. When a nucleotide, for example a C, is added to a DNA template and is then incorporated into a strand of DNA, a hydrogen ion will be released. The charge from that ion will change the pH of the solution, which can be detected by Ion Torrent's ion sensor. The sequencer—essentially the world's smallest solid-state pH meter—calls the base, going directly from chemical information to digital information. The Ion personal Genome Machine (PGM.TM.) sequencer then sequentially floods the chip with one nucleotide after another. If the next nucleotide that floods the chip is not a match, no voltage change will be recorded and no base will be called. If there are two identical bases on the DNA strand, the voltage will be double, and the chip will record two identical bases called. Direct detection allows recordation of nucleotide incorporation in seconds.

In another embodiment, the present method includes obtaining sequence information for the nucleic acids in the test sample, using sequencing by hybridization. Sequencing-by-hybridization includes contacting the plurality of polynucleotide sequences with a plurality of polynucleotide probes, wherein each of the plurality of polynucleotide probes can be optionally tethered to a substrate. The substrate might be flat surface including an array of known nucleotide sequences. The pattern of hybridization to the array can be used to determine the polynucleotide sequences present in the sample. In other embodiments, each probe is tethered to a bead, e.g., a magnetic bead or the like. Hybridization to the beads can be determined and used to identify the plurality of polynucleotide sequences within the sample.

In some embodiments of the methods described herein, the sequence reads are about 20 bp, about 25 bp, about 30 bp, about 35 bp, about 40 bp, about 45 bp, about 50 bp, about 55 bp, about 60 bp, about 65 bp, about 70 bp, about 75 bp, about 80 bp, about 85 bp, about 90 bp, about 95 bp, about 100 bp, about 110 bp, about 120 bp, about 130, about 140 bp, about 150 bp, about 200 bp, about 250 bp. In some embodiments, paired end reads are used to determine sequences of interest, which include sequence reads that are about 20 bp to 250 bp, about 50 bp to 200 bp, or 80 bp to 150 bp. In various embodiments, the paired end reads are used to evaluate both a TUMI sequence and a sample index sequence that are positioned apart from each other on opposite ends of the targeted nucleotide region of interest, with directional sequencing at both ends that proceeds away from the targeted nucleotide region of interest.

Systems for Sequencing Using TUMIs

Analysis of the sequencing data and the diagnosis derived therefrom may be performed using various computer executed algorithms and programs. Therefore, certain embodiments employ processes involving data stored in or transferred through one or more computer systems or other processing systems. Embodiments disclosed herein also relate to apparatus for performing these operations. This apparatus may be specially constructed for the required purposes, or it may be a general-purpose computer (or a group of computers) selectively activated or reconfigured by a computer program and/or data structure stored in the computer. In some embodiments, a group of processors performs some or all of the recited analytical operations collaboratively (e.g., via a network or cloud computing) and/or in parallel. A processor or group of processors for performing the methods described herein may be of various types including microcontrollers and microprocessors such as programmable devices (e.g., CPLDs and FPGAs) and non-programmable devices such as gate array ASICs or general purpose microprocessors.

One implementation provides a system including a sequencer for receiving a nucleic acid sample and providing nucleic acid sequence information from the sample; a processor; and a machine readable storage medium having stored thereon instructions for execution on said processor to determine a sequence of interest (such as the TUMI sequence) in the test sample. The instructions may include: (a) applying adapters (via a PCR primer strand or strands) to both ends of DNA fragments in the sample, wherein the adapters each include a double-stranded hybridized region, a single-stranded 5' arm, a single-stranded 3' arm, and a TUMI on one strand or each strand of the adapters, thereby obtaining DNA-adapter products; (b) amplifying the DNA-adapter products to obtain a plurality of amplified polynucleotides; (c) sequencing the plurality of amplified polynucleotides, thereby obtaining a plurality of reads associated with a plurality of TUMIs; (d) identifying the TUMI present in the samples and (e) from the identified TUMIs, determining whether the targeted nucleotide region of interest (such as a particular transgene) is present in the sample without obtaining the sequence of the targeted nucleotide region of interest.

In another implementation, the instructions includes: (a) applying adapters (via a PCR primer strand or strands) to both ends of double-stranded DNA fragments in the sample, wherein the adapters each include a double-stranded hybridized region, a single-stranded 5' arm, a single-stranded 3' arm, and a TUMI on one strand or each strand of the adapters, wherein the TUMI can be combined with other information, such as a sample index, to uniquely identify an individual molecule of the double-stranded DNA fragments; (b) amplifying both strands of the DNA-adapter products to obtain a plurality of amplified polynucleotides; (c) sequencing the plurality of amplified polynucleotides, thereby obtaining a plurality of reads each associated with a TUMI; and (d) identifying one or more targeted nucleotide regions of interest (such as a transgene) associated with the identified TUMI sequences.

In some embodiments of any of the systems provided herein, the sequencer is configured to perform next generation sequencing (NGS). In some embodiments, the sequencer is configured to perform massively parallel sequencing using sequencing-by-synthesis with reversible dye terminators. In other embodiments, the sequencer is configured to perform sequencing-by-ligation. In yet other embodiments, the sequencer is configured to perform single molecule sequencing.

In addition, certain embodiments relate to tangible and/or non-transitory computer readable media or computer program products that include program instructions and/or data (including data structures) for performing various computer-implemented operations. Examples of computer-readable media include, but are not limited to, semiconductor memory devices, magnetic media such as disk drives, magnetic tape, optical media such as CDs, magneto-optical media, and hardware devices that are specially configured to store and perform program instructions, such as read-only memory devices (ROM) and random access memory (RAM). The computer readable media may be directly controlled by an end user or the media may be indirectly controlled by the end user. Examples of directly controlled media include the media located at a user facility and/or media that are not shared with other entities. Examples of indirectly controlled media include media that is indirectly accessible to the user via an external network and/or via a service providing shared resources such as the "cloud." Examples of program instructions include both machine code, such as produced by a compiler, and files containing higher level code that may be executed by the computer using an interpreter.

In various embodiments, the data or information employed in the disclosed methods and apparatus is provided in an electronic format. Such data or information may include reads and tags derived from a nucleic acid sample, reference sequences (including reference sequences providing solely or primarily polymorphisms), calls such as TUMI association, sample index association and the like. As used herein, data or other information provided in electronic format is available for storage on a machine and transmission between machines. Conventionally, data in electronic format is provided digitally and may be stored as bits and/or bytes in various data structures, lists, databases, etc. The data may be embodied electronically, optically, etc.

One embodiment provides a computer program product for generating an output indicating the identify of all transgenes present in a plant or seed test sample. The computer product may contain instructions for performing any one or more of the above-described methods for determining the sequence of a TUMI and a corresponding targeted nucleotide region of interest. As explained, the computer product may include a non-transitory and/or tangible computer readable medium having a computer executable or compilable logic (e.g., instructions) recorded thereon for enabling a processor to determine a sequence of interest. In one example, the computer product includes a computer readable medium having a computer executable or compilable logic (e.g., instructions) recorded thereon for enabling a processor to diagnose a condition or determine a nucleic acid sequence of interest.

Another implementation provides a computer program product including a non-transitory machine readable medium storing program code that, when executed by one or more processors of a computer system, causes the computer system to implement a method for determining the identity of all transgenic sequences of a plant or seed test sample. The program code may include: (a) code for applying an adapter (for example, as part of a PCR primer strand), to one or both ends of DNA fragments in the sample, wherein the adapter includes a TUMI, and obtaining an amplicon comprising the TUMI; (b) code for amplifying the amplicon to obtain a plurality of amplicons; (c) code for sequencing the plurality of amplicons, thereby obtaining a plurality of reads associated with a plurality of TUMI; (d) code for associated the TUMI reads with a transgene, and (e) code for identifying the transgene present in each plant or seed test sample, all without requiring the direct sequence of the transgene.

In some embodiments, the instructions may further include automatically recording information pertinent to the method, such as seed or grain tracing information. The seed or grain tracking information may be updated into a database that tracks such seed or grain. Further, based on the results of the processor-implemented analysis, the method may further involve keeping, discarding or identity preserving the test sample.

These various types of data may be obtained, stored transmitted, analyzed, and/or manipulated at one or more locations using distinct apparatus. The processing options span a wide spectrum. At one end of the spectrum, all or much of this information is stored and used at the location where the test sample is processed, e.g., a seed lab, grain elevator, shipping container, etc. In other extreme, the sample is obtained at one location, it is processed and optionally sequenced at a different location, reads are aligned and calls are made at one or more different locations, and any action needed to be taken with regard to the sample are taken at still another location.

Figure 4:
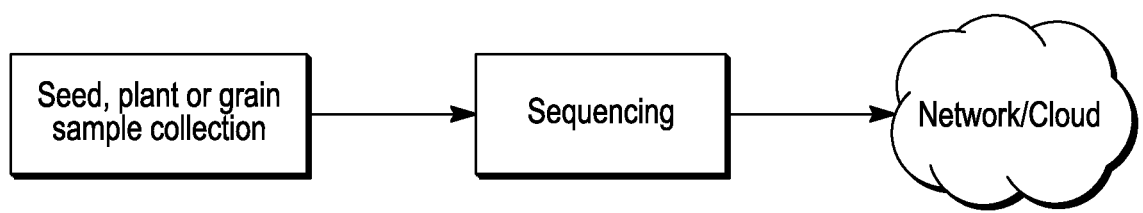
FIG. 4 Illustrates one implementation of an integrated seed or grain tracking system for detecting transgenes in a seed, plant or grain produced from the plant.

FIG. 4 shows one implementation of an integrated seed or grain tracking system for detecting transgenes in a seed, plant or grain produced from the plant. A sample collection location is used for obtaining a test sample from the seed, plant or grain. The sample is then provided to a sequencing location where the test sample may be processed and sequenced as described herein, which location includes apparatus for processing and sequencing the sample. The result of the sequencing, which is described elsewhere herein, is provided in an electronic format to a network such as a network or cloud. Once present on the network or cloud, the data may be viewed, utilized and updated by any number of users, including farmers, elevators, grain shippers and seed companies. This is one of many variations on how the various operations associated with determining the presence or absence of a transgene or other targeted nucleotide region of interest may be divided among various locations. One common variant involves providing sample collection and processing and sequencing in a single location. Another variation involves providing processing and sequencing at the same location as analysis and call generation.

What is claimed:

1. A method for detecting a target nucleotide region of interest in a plant genome, wherein the plant genome is from wheat, potato, cotton, apple, alfalfa or canola, by directional nucleotide sequencing, the method comprising:

providing a first polynucleotide fragment comprising a first polynucleotide PCR primer sequence specific to the target nucleotide region of interest, a sequencing primer binding site sequence, and a polynucleotide sequence region uniquely associated with the target nucleotide region of interest, wherein the sequencing primer binding site is positioned between the polynucleotide sequence uniquely associated with the target nucleotide region of interest and the first polynucleotide PCR primer sequence specific to the target nucleotide region of interest;

providing a second polynucleotide fragment comprising a second polynucleotide PCR primer sequence specific to the target nucleotide region of interest;

performing a PCR to create one or more amplicons comprising the sequencing primer binding site sequence, the polynucleotide sequence uniquely associated with the target nucleotide region of interest, and the target nucleotide region of interest;

sequencing the one or more amplicons using the sequencing primer in a direction away from the target nucleotide region of interest so that the polynucleotide sequence uniquely associated with the target nucleotide region of interest is sequenced and the target nucleotide region of interest in the one or more amplicons is not sequenced; and detecting the target nucleotide region in the plant genome based on the sequence information of the polynucleotide sequence uniquely associated with the target nucleotide region of interest.

2. The method of claim 1, wherein the target nucleotide region of interest is a transgene.

3. The method of claim 2, wherein the transgene confers herbicide tolerance.

4. The method of claim 2, wherein the transgene confers disease resistance.

5. The method of claim 2, wherein the transgene confers insect resistance.

6. The method of claim 1, wherein sequencing adapters are attached to the ends of the one or more amplicons through a second PCR reaction performed prior to the sequencing reaction.

7. The method of claim 1, wherein one or more sample indices are present on the one or more amplicons, wherein the one or more sample indices are added to at least one of the first polynucleotide fragment and the second polynucleotide fragment, or are added to the amplicons comprising the sequencing primer binding site sequence, the polynucleotide sequence uniquely associated with the target nucleotide region of interest, and the target nucleotide region of interest by a subsequent round of PCR.

8. The method of claim 1, wherein at least one of the first polynucleotide PCR primer sequence specific to the target nucleotide region of interest and the second polynucleotide PCR primer sequence specific to the target nucleotide region of interest hybridizes to a sequence that spans a border sequence between genomic DNA and the target nucleotide region of interest.

9. The method of claim 1, wherein at least one of the first polynucleotide PCR primer sequence specific to the target nucleotide region of interest and the second polynucleotide PCR primer sequence specific to the target nucleotide region of interest hybridizes to a sequence within the target nucleotide region of interest.

10. The method of claim 1, wherein the target nucleotide region of interest comprises a single nucleotide polymorphism.

11. The method of claim 1, wherein the target nucleotide region of interest comprises an introduced site-specific genome modification.

12. The method of claim 1, wherein the target nucleotide region of interest comprises an allelic variation or a haplotype.

13. The method of claim 1, wherein adapter oligonucleotides that are complementary to flow-cell anchor oligonucleotides are added to the one or more amplicons by a second round of PCR.

14. The method of claim 13, wherein prior to the second round of PCR, primer dimers are reduced by a purification or selection step.

15. The method of claim 1, wherein the PCR is quantitative.

16. The method of claim 1, wherein more than one polynucleotide sequence region uniquely associated with a nucleotide region of interest is utilized, and each such polynucleotide sequence region uniquely associated with a target nucleotide region of interest has a Hamming distance of at least 4 from each other such sequence.

17. The method of claim 1, further comprising the detection of a genomic marker region comprising the steps of:

during the PCR reaction, also creating one or more amplicons each comprising a genomic marker region, wherein an additional sequencing primer binding site is positioned on the amplicon proximal to the genomic marker region; and sequencing the one or more amplicons using an additional sequencing primer, wherein the additional sequencing primer binding site is positioned such that the additional sequencing primer will direct sequencing to occur toward and through the genomic marker region.

18. The method of claim 17, wherein the genomic marker region comprises one or more SNP markers.

19. The method of claim 1, wherein the plant genome is from wheat.

20. The method of claim 1, wherein the plant genome is from canola.

21. The method of claim 1, wherein the target nucleotide region of interest is a CRISPR modified trait.

* * * * *